United States Patent
Ogawa et al.

(10) Patent No.: US 10,028,903 B2
(45) Date of Patent: Jul. 24, 2018

(54) ACTIVE AGENT LOADED UNIFORM, RIGID, SPHERICAL, NANOPOROUS CALCIUM PHOSPHATE PARTICLES AND METHODS OF MAKING AND USING THE SAME

(71) Applicant: Laboratory Skin Care, Inc., Tahoe City, CA (US)

(72) Inventors: Tetsuro Ogawa, Mitaka (JP); Akira Yamamoto, Kyoto (JP)

(73) Assignee: Laboratory Skin Care, Inc., Redwood City, CA (US)

(*) Notice: Subject to any disclaimer, the term of this patent is extended or adjusted under 35 U.S.C. 154(b) by 0 days.

(21) Appl. No.: 13/966,637

(22) Filed: Aug. 14, 2013

(65) Prior Publication Data

US 2014/0199400 A1    Jul. 17, 2014

Related U.S. Application Data

(63) Continuation of application No. 12/565,687, filed on Sep. 23, 2009, now Pat. No. 8,535,723.

(Continued)

(51) Int. Cl.
  *A61K 9/00*   (2006.01)
  *A61Q 19/00*   (2006.01)
(Continued)

(52) U.S. Cl.
  CPC .......... *A61K 9/0014* (2013.01); *A61K 8/0279* (2013.01); *A61K 8/24* (2013.01);
(Continued)

(58) Field of Classification Search
  None
  See application file for complete search history.

(56) References Cited

U.S. PATENT DOCUMENTS

| 4,218,255 A |   | 8/1980  | Bajpai et al. |
|---|---|---|---|
| 5,055,307 A | * | 10/1991 | Tsuru .................. A61K 9/1611 424/493 |

(Continued)

FOREIGN PATENT DOCUMENTS

| CN | 1843902 A | 10/2006 |
|---|---|---|
| JP | 7-330319 A | 12/1995 |

(Continued)

OTHER PUBLICATIONS

Buprenorphine. Accessed online on Apr. 2, 2015 at http://www.drugbank.ca/drugs/DB00921#properties.*

(Continued)

*Primary Examiner* — Carlos A Azpuru
*Assistant Examiner* — Casey S Hagopian
(74) *Attorney, Agent, or Firm* — Bret E. Field; Bozicevic, Field & Francis LLP

(57) ABSTRACT

Uniform, rigid, spherical nanoporous calcium phosphate particles that define an internal space and an amount of active agent present in the internal space are provided. Also provided are topical delivery compositions that include the active agent loaded particles, as well as methods of making the particles and topical compositions. The particles and compositions thereof find use in a variety of different applications, including active agent delivery applications.

16 Claims, 5 Drawing Sheets

Related U.S. Application Data

(60) Provisional application No. 61/099,500, filed on Sep. 23, 2008.

(51) Int. Cl.

| | | |
|---|---|---|
| *A61K 8/24* | (2006.01) | |
| *A61K 8/02* | (2006.01) | |
| *A61K 8/368* | (2006.01) | |
| *A61K 9/16* | (2006.01) | |
| *A61K 31/216* | (2006.01) | |
| *A61K 31/60* | (2006.01) | |
| *A61K 9/14* | (2006.01) | |
| *A61K 31/05* | (2006.01) | |
| *A61K 47/02* | (2006.01) | |
| *A61K 31/23* | (2006.01) | |
| *A61K 31/66* | (2006.01) | |

(52) U.S. Cl.
CPC .............. *A61K 8/368* (2013.01); *A61K 9/143* (2013.01); *A61K 9/1611* (2013.01); *A61K 31/05* (2013.01); *A61K 31/216* (2013.01); *A61K 31/23* (2013.01); *A61K 31/60* (2013.01); *A61K 31/66* (2013.01); *A61K 47/02* (2013.01); *A61Q 19/008* (2013.01); *A61K 2800/56* (2013.01); *Y10S 977/773* (2013.01); *Y10S 977/906* (2013.01)

(56) References Cited

U.S. PATENT DOCUMENTS

| | | |
|---|---|---|
| 5,158,756 A | 10/1992 | Ogawa et al. |
| 6,096,324 A | 8/2000 | Mansouri |
| 6,416,774 B1 * | 7/2002 | Radin et al. .................. 424/408 |
| 2001/0006680 A1 | 7/2001 | Mansouri |
| 2002/0086055 A1 | 7/2002 | Wong et al. |
| 2003/0077235 A1 | 4/2003 | Mansouri |
| 2005/0123611 A1 | 6/2005 | Barbe et al. |
| 2005/0271694 A1 | 12/2005 | Mansouri et al. |
| 2006/0073205 A1 * | 4/2006 | Ohta et al. .................. 424/471 |
| 2006/0093670 A1 | 5/2006 | Mizushima et al. |
| 2006/0193879 A1 | 8/2006 | Mansouri |
| 2006/0257492 A1 * | 11/2006 | Wen ........................ A61K 33/42 424/489 |
| 2008/0160088 A1 * | 7/2008 | Mackowiak ............. A61K 8/19 424/489 |
| 2009/0074688 A1 | 3/2009 | Mansouri |
| 2009/0104133 A1 | 4/2009 | Mansouri |

FOREIGN PATENT DOCUMENTS

| | | |
|---|---|---|
| JP | 2005-47893 A | 2/2005 |
| JP | 2007-1865 A | 1/2007 |
| WO | WO 1996/041611 A1 | 12/1996 |
| WO | WO 9641611 A1 * | 12/1996 ............... A61K 8/24 |
| WO | WO2004112751 A1 | 12/2004 |
| WO | WO 2005/084637 A2 | 9/2005 |
| WO | WO2010039560 A2 | 4/2010 |
| WO | WO 2010/129819 A2 | 11/2010 |

OTHER PUBLICATIONS

Fentanyl. Accessed online on Apr. 2, 2015 at www.swgdrug.org/Monographs/FENTANYL.pdf.*

Retinol. Sigma Aldrich data sheet. Accessed online on Sep. 4, 2015 at https://www.sigmaaldrich.com/content/dam/sigma-aldrich/docs/Sigma/Datasheet/6/95144dat.pdf.*

Retinol. Sigma Aldrich data sheet. Accessed online on Sep. 4, 2015 at https://www.sigmaaldrich.com/contentJdam/sigma-aldrich/docs/Sig ma/Datasheet/6/95144dat.pdf.*

* cited by examiner

ACTIVE AGENT LOADED UNIFORM, RIGID, SPHERICAL, NANOPOROUS CALCIUM PHOSPHATE PARTICLES AND METHODS OF MAKING AND USING THE SAME

CROSS-REFERENCE TO RELATED APPLICATIONS

Pursuant to 35 U.S.C. § 119 (e), this application claims priority to the filing date of U.S. Provisional Patent Application Ser. No. 61/099,500 filed Sep. 23, 2008; the disclosure of which application is herein incorporated by reference.

INTRODUCTION

A variety of different active agents have been and continue to be developed for use in the treatment of a variety of different conditions, including both disease and non-disease conditions. For such applications, an effective amount of the active agent must be delivered to the subject in need thereof. A variety of different delivery formulations and routes have been developed, where such routes may vary depending on the nature of the active agent, the identity of the subject to which the active agent is to be administered, etc. Typically, less invasive delivery routes are better tolerated and therefore are more desirable.

One type of delivery route that is of great interest because of its minimally invasive nature is dermal delivery. In dermal delivery, an active agent composition is applied to a skin site to deliver the active agent to the subject. Many dermal delivery technologies currently in use or under evaluation are not entirely satisfactory. For example, certain dermal delivery technologies may disrupt the integrity of the stratum corneum (Sc) and/or rely on the presence of permeation enhancers, which can cause unwanted damage and/or irritation. In addition, certain dermal delivery technologies may be polymer- and/or liposome based technologies, neither of which technologies truly delivers through the Sc. Furthermore these technologies cannot be applied to large molecular weight bio-actives.

As such, there continues to be a need for the development of new dermal delivery technologies which overcome one or more of the disadvantages experiences with current dermal delivery approaches.

SUMMARY

Uniform, rigid, spherical nanoporous calcium phosphate particles that define an internal space and an amount of active agent present in the internal space are provided. Also provided are topical delivery compositions that include the active agent loaded particles, as well as methods of making the particles and topical compositions. The particles and compositions thereof find use in a variety of different applications, including active agent delivery applications.

DETAILED DESCRIPTION

Figure 1A:
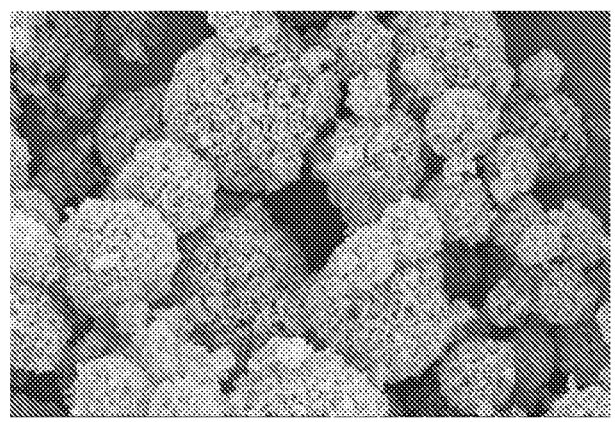
FIGS. 1A to 2B provide scanning electron microscope images of uniform, rigid, spherical, nanoporous calcium phosphate particles that find use in delivery compositions of the invention.

Uniform, rigid, spherical nanoporous calcium phosphate particles that define an internal space and an amount of active agent present in the internal space are provided. Also provided are topical delivery compositions that include the active agent loaded particles, as well as methods of making the particles and topical compositions. The particles and compositions thereof find use in a variety of different applications, including active agent delivery applications.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Active Agent Loaded Uniform, Rigid, Spherical, Nanoporous Calcium Phosphate Particles As summarized above, aspects of the invention include active agent loaded uniform, rigid, spherical, nanoporous calcium phosphate particles. The active agent loaded particles are calcium phosphate particles that include a porous structure, as described in greater detail below. The porous structure of the particles is such that for each particle, the porosity of the particle defines an internal space. The internal space is a void area or volume located inside of the particle and is configured such that it can contain an amount of active agent. In active agent loaded particles of the invention, an amount of active agent is present in the internal space, such that the amount of active agent is located inside of particle, as opposed to present on the outer surface of the particle. Particles of the invention having an internal amount of active may or may not include active agent that is present on, e.g., absorbed onto, the surface of the particle.

The amount of internal active agent present in particles of the composition may vary. In certain embodiments, the amount of internal active agent is 2% or more, e.g., 4% or more, 5% or more, 7.5% or more, 10% or more, 15% or more, including 20% or more by weight of the particle that includes the internal active agent. As such, in some instances the amount of active agent present in the internal space of a given particle is 10% by weight or more of the calcium phosphate particle.

The uniform, rigid, spherical, nanoporous calcium phosphate particles are uniform and spherical in shape. By "uniform" is meant that the shape of the particles does not vary substantially, such that the particles have the substantially the same spherical shape. By "rigid" is meant that the particles are hard, such that they are not pliant. The term "spherical" is employed in its conventional sense to mean a round body whose surface is at all points substantially equidistant from the center. Of interest are calcium phosphate particles in which the median diameter is 20 µm or less, such as 10 µm or less; including 5 µm or less, where in some instances the medium diameter is 4 µm or less, such as 3 µm or less, including 2 µm or less.

The particles are nanoporous. By "nanoporous" is meant that the particles have a porosity of 30% or more, such as 40% or more, including 50% or more, where the porosity may range from 30% to 85%, such as from 40% to 70%, including from 45% to 55%, as determined using a mercury intrusion porosimeter porosity determination protocol as described in ASTM D 4284-88 "Standard Test Method for Determining Pore Volume Distribution of Catalysts by Mercury Intrusion Porosimetry". Porosity is also described by "pore volume (ml/g)" and in such instances many range from 0.1 ml/g to 2.0 ml/g. In some cases, the particles have a porosity such that their internal surface area ranges from 10 $m^2/g$ to 150 $m^2/g$, such as from 20 $m^2/g$ to 100 $m^2/g$, including 30 $m^2/g$ to 80 $m^2/g$, as determined using a BET gas adsorption surface area determination protocol as described in ASTM D3663-03 Standard Test Method for Surface Area of Catalysts and Catalyst Carriers. The pore diameter may vary, ranging in certain instances from 2 to 100 nm, such as 5 to 80 nm, including 10 to 60 nm. In addition, the particles may have a tapping density ranging from 0.2 $g/cm^3$ to 0.5 $g/cm^3$, such as from 0.25 $g/cm^3$ to 0.45 $g/cm^3$, including from 0.3 $g/cm^3$ to 0.4 $g/cm^3$. The tap density can be measured by using standard ASTM WK13023—New Determination of Tap Density of Metallic Powders by a Constant Volume Measuring Method.

The particles are, in some instances, chemically pure. By chemically pure is meant that the particles are made up of substantially one type of calcium phosphate mineral. In some instances, the calcium phosphate particles are made up of a calcium phosphate that is described by the molecular formula $Ca_{10}(PO_4)_6(OH)_2$.

In some instances, the particles are ceramic particles. By ceramic is meant that the particles are produced using a method which includes a step of subjecting the particles to high temperature conditions, where such conditions are illustrated below. High temperatures may range from 200 to 1000° C., such as 300 to 900° C. and including 300 to 800° C. In some embodiments, the particles have a compression rupture strength ranging from 20 to 200 MPa, such as from 50 to 150 MPa, and including 75 to 90 MPa, as determined using a SHIMADZU MCT-W500 micro-compression testing machine particle strength determination protocol with a particle sintered at temperature of 400° C. to 900° C., as described in European Patent EP1840661. In some embodiments, the particles are biodegradable, by which is meant that the particles degrade in some manner, e.g., dissolve, over time under physiological conditions. As the particles of these embodiments are biodegradeable under physiological conditions, they at least begin to dissolve at a detectable rate under conditions of pH of 6 or less, such as 5.5 or less, including 5 or less.

The uniform, rigid, spherical, nanoporous calcium phosphate particles of the delivery compositions of the invention may be prepared using any convenient protocol. In one protocol of interest, the particles are manufactured by spray drying a slurry that includes nano calcium phosphate (e.g., hydroxyapatite) crystals (which may range from 2 nm to 100 nm size range) to produce uniform spherical nanoporous calcium phosphate particles. The resultant particles are then sintered for a period of time sufficient to provide mechanically and chemically stable rigid spheres. In this step, the sintering temperatures may range from 200° C. to 1000° C., such as 300° C. to 900° C. and including 300° C. to 800° C. for a period of time ranging from 1 hour to 10 hours, such as 2 hours to 8 hours and including 3 hours to 6 hours.

As summarized above, active agent loaded uniform, rigid, spherical, nanoporous calcium phosphate particles include an amount of an active agent component (made of a single type of active agent or two or more different types of active agents) present in an internal space of the particle, as described above. The term "active agent" refers to any compound or mixture of compounds which produces a physiological result, e.g., a beneficial or useful result, upon contact with a living organism, e.g., a mammal, such as a human. Active agents are distinguishable from other components of the delivery compositions, such as carriers, diluents, lubricants, binders, colorants, etc. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication.

The active agent is a compound that interacts with a target in a living subject. The target may be a number of different types of naturally occurring structures, where targets of interest include both intracellular and extra-cellular targets. Such targets may be proteins, phospholipids, nucleic acids and the like. The active agent may include one or more functional groups necessary for structural interaction with the target, e.g., groups necessary for hydrophobic, hydrophilic, electrostatic or even covalent interactions, depending on the particular active agent and its intended target, where functional groups of interest include groups that participate in hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Active agents of interest may include cyclical carbon or heterocyclic structures and/or aromatic or polyaromatic structures substituted with one or more of the above functional groups. Also of interest as moieties of active agents are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The active agents may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the active agent may be obtained from a library of naturally occurring or synthetic molecules, including a library of compounds produced through combinatorial means, i.e., a compound diversity combinatorial library. When obtained from such libraries, the active agent employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc. Active agents of interest include, but are not limited to:

antibiotics, such as: aminoglycosides, e.g. amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol; ansamycins, e.g. rifamide, rifampin, rifamycin, rifapentine, rifaximin; b-lactams, e.g. carbacephems, carbapenems, cephalosporins, cehpamycins, monobactams, oxaphems, penicillins; lincosamides, e.g. clinamycin, lincomycin; macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, minocycline, etc.; synthetic antibacterial agents, such as 2,4-diaminopyrimidines, nitrofurans, quinolones and analogs thereof, sulfonamides, sulfones;

antifungal agents, such as: polyenes, e.g. amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole;

anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

antiprotozoan agents, such as: acranil, tinidazole, ipronidazole, ethylstibamine, pentamidine, acetarsone, aminitrozole, anisomycin, nifuratel, tinidazole, benzidazole, suramin;

cardioprotective agents, e.g., Zinecard (dexrazoxane); blood modifiers, including anticoagulants (e.g., coumadin (warfarin sodium), fragmin (dalteparin sodium), heparin, innohep (tinzaparin sodium), lovenox (enoxaparin sodium), orgaran (danaparoid sodium)) antiplatelet agents (e.g., aggrasta (tirofiban hydrochloride), aggrenox (aspirin/extended release dipyridamole), agrylin (anagrelide hydrochloride), ecotrin (acetylsalicylic acid), folan (epoprostenol sodium), halfprin (enteric coated aspirin), integrillin (eptifibatide), persantine (dipyridamole USP), plavix (clopidogrel bisulfate), pletal (cilostazol), reopro (abciximab), ticlid (ticlopidine hydrochloride)), thrombolytic agents (activase (alteplase), retavase (reteplase), streptase (streptokinase)); adrenergic blockers, such as cardura (doxazosin mesylate), dibenzyline (phenoxybenzamine hydrochloride), hytrin (terazosin hydrochloride), minipress (prazosin hydrochloride), minizide (prazosin hydrochloride/polythiazide); adrenergic stimulants, such as aldoclor (methyldopa-chlorothiazide), aldomet (methyldopa, methyldopate HCl), aldoril (methyldopa-hydrochlorothiazide), catapres (clonidine hydrochloride USP, clonidine), clorpres (clonidine hydrochloride and chlorthalidone), combipres (clonidine hydrochloride/chlorthalidone), tenex (guanfacine hydrochloride); alpha/bet adrenergic blockers, such as coreg (carvedilol), normodyne (labetalol hydrochloride); angiotensin converting enzyme (ACE) inhibitors, such as accupril (quinapril hydrochloride), aceon (perindopril erbumine), altace (ramipril), captopril, lotensin (benazepril hydrochloride), mavik (trandolapril), monopril (fosinopril sodium tablets), prinivil (lisinopril), univasc (moexipril hydrochloride), vasotec (enalaprilat, enalapril maleate), zestril (lisinopril); angiotensin converting enzyme (ACE) inhibitors with calcium channel blockers, such as lexxel (enalapril maleate felodipine ER), lotrel (amlodipine and benazepril hydrochloride), tarka (trandolapril/verapamil hydrochloride ER); angiotensin converting enzyme (ACE) inhibitors with diuretics, such as accuretic (quinapril HCl/hydroclorothiazide), lotensin (benazepril hydrochloride and hydrochlorothiazide USP), prinizide (lisinopril-hydrochlorothiazide), u niretic (moexipril hydrochloride/hydrochlorothiazide), vaseretic (enalapril maleate-hydrochlorothiazide), zestoretic (lisinopril and hydrochlorothiazide); angiotensin II receptor antagonists, such as atacand (candesartan cilexetil), avapro (irbesartan), cozaar (losartan potassium), diovan (valsartan), micardis (telmisartan), teveten (eprosartan mesylate); angiotensin II receptor antagonists with diuretics, such as avalide (irbesartan-hydrochlorothiazide), diovan (valsartan and hydrochlorothiazide), hyzaar (losartan potassium-hydrochlorothiazide); antiarrhythmics, such as Group I (e.g., mexitil (mexiletine hydrochloride, USP), norpace (disopyramide phosphate), procanbid (procainamide hydrochloride), quinaglute (quinidine gluconate), quinidex (quinidine sulfate), quinidine (quinidine gluconate injection, USP), rythmol (propafenone hydrochloride), tambocor (flecainide acetate), tonocard (tocainide HCl)), Group II (e.g., betapace (sotalol HCl), brevibloc (esmolol hydrochloride), inderal (propranolol hydrochloride), sectral (acebutolol hydrochloride)), Group III (e.g., betapace (sotalol HCl), cordarone (amiodarone hydrochloride), corvert (ibutilide fumarate injection), pacerone (amiodarone HCl), tikosyn (dofetilide)), Group IV (e.g., calan (verapamil hydrochloride), cardizem (diltiazem HCl), as well as adenocard (adenosine), lanoxicaps (digoxin), lanoxin (digoxin)); antilipemic acids, including bile acid sequestrants (e.g., colestid (micronized colestipol hydrochloride), weichol (colesevelam hydrochloride)), fibric acid derivatives (e.g., atromid (clofibrate), lopid (gemfibrozal tablets, USP), tricor (fenofibrate capsules)), HMG-CoA reductase inhibitors (e.g., baycol (cerivastatin sodium tablets), lescol (fluvastatin sodium), lipitor (atorvastatin calcium), mevacor (lovastatin), pravachol (pravastatin sodium), zocor (simvastatin)), Nicotinic Acid (e.g., Niaspan (niacin extended release tablets)); beta adrenergic blocking agents, e.g., betapace (sotalol HCl), blocadren (timolol maleate), brevibloc (esmolol hydrochloride), cartrol (carteolol hydrochloride), inderal (propranolol hydrochloride), kerlone (betaxolol hydrochloride), nadolol, sectral (acebutolol hydrochloride), tenormin (atenolol), toprol (metoprolol succinate), zebeta (bisoprolol fumarate); beta adrenergic blocking agents with diuretics, e.g., corzide (nadolol and bendroflumethiazide tablets), inderide (propranolol hydrochloride and hydroclorothiazide), tenoretic (atenolol and chlorthalidone), timolide (timolol maleate-hydrochlorothiazide), ziac (bisoprolol fumarate and hydrochlorothiazide); calcium channel blockers, e.g., adalat (nifedipine), calan (verapamil hydrochloride), cardene (nicardipine hydrochloride), cardizem (diltiazem HCl), covera (verapamil hydrochloride), isoptin (verapamil hydrochloride), nimotop (nimodipine), norvasc (amlodipine besylate), plendil (felodipine), procardia (nifedipine), sular (nisoldipine), tiazac (diltiazem hydrochloride), vascor (bepridil hydrochloride), verelan (verapamil hydrochloride); diuretics, including carbonic anhydrase inhibitors (e.g., daranide (dichlorphenamide)), combination diuretics (e.g., aldactazide (spironolactone with hydrochlorothiazide), dyazide (triamterene and hydrochlorothiazide), maxzide (triamterene and hydrochlorothiazide), moduretic (amiloride HCl-hydrochlorothiazide)), loop diuretics (demadex (torsemide), edecrin (ethacrynic acid, ethacrynate sodium), furosemide), potassium-sparing diuretics (aldactone (spironolactone), dyrenium (triamterene), midamor (amiloride NCl)), thiazides & related diuretics (e.g., diucardin (hydroflumethiazide), diuril (chlorothiazide, chlorothiazide sodium), enduron (methyclothiazide), hydrodiuril hydrochlorothiazide), indapamide, microzide (hydrochlorothiazide) mykrox (metolazone tablets), renese (polythi-azide), thalitone (chlorthalidone, USP), zaroxolyn (metolazone)); inotropic agents, e.g., digitek (digoxin), dobutrex (dobutamine), lanoxicaps (digoxin), lanoxin (digoxin), primacor (milrinone lactate); activase (alteplase recombinant); adrenaline chloride (epinephrine injection, USP); demser (metyrosine), inversine (mecamylamine HCl), reopro (abciximab), retavase (reteplase), streptase (streptokinase), tnkase (tenecteplase); vasodilators, including coronary vasodilators (e.g., imdur (isosorbide mononitrate), ismo (isosorbide mononitrate), isordil (isosorbide dinitrate), nitrodur (nitroglycerin), nitrolingual (nitroglycerin lingual spray), nitrostat (nitroglycerin tablets, USP), sorbitrate (isosorbide dinitrate)), peripheral vasodilators & combinations (e.g., corlopam (fenoldopam mesylate), fiolan (epoprostenol sodium), primacor (milrinone lactate)), vasopressors, e.g., aramine (metaraminol bitartrate), epipen (EpiPen 0.3 mg brand of epinephrine auto injector, EpiPen Jr. 0.15 mg brand of epinephrine auto injector), proamatine (midodrine hydrochloride); etc.

psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g. anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g. central antitussives (opium alkaloids and their derivatives);

pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g.

spasmolytics (anticholinergics, musculotropic spasmolytics), vasodilators, smooth muscle stimulants, (4) histamines and antihistamines, e.g. histamine and derivative thereof (betazole), antihistamines (H1-antagonists, H2-antagonists), histamine metabolism drugs, (5) cardiovascular drugs, e.g. cardiotonics (plant extracts, butenolides, pentadienolids, alkaloids from erythrophleum species, ionophores, -adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g. antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs;

chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g. Vincristine (Oncovin), Vinblastine (Velban, Velbe), Paclitaxel (Taxol), and the like; antimetabolites, e.g. Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g. Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like.

Drug compounds of interest are also listed in: Goodman & Gilman's, The Pharmacological Basis of Therapeutics (9th Ed) (Goodman et al. eds) (McGraw-Hill) (1996); and 2001 Physician's Desk Reference.

Specific categories and examples of active agents include, but are not limited to: those appearing the following table:

| Therapeutic Category | Pharmacological Class | Structural Examples |
|---|---|---|
| Analgesics | Opioid Analgesics | Includes drugs such as Morphine, Meperidine and Propoxyphene |
| | Non-opioid Analgesics | Includes drugs such as Sodium Salicylate, Diflunisal, Para-Aminophenol Derivatives, Anthranilic Acid Derivatives, and Phenylpropionic Acid Derivatives |
| Anesthetics | | |
| Antibacterials | Beta-lactam, Cephalosporins | |
| | Beta-lactam, Penicillins | |
| | Beta-lactam, Other | Includes drugs such as Loracarbef |
| | Macrolides | |
| | Quinolones | |
| | Sulfonamides | |
| | Tetracyclines | |
| | Antibacterials, Other | Includes drugs such as Trimethoprim, Vancomycin, Lincomycin, Clindamycin, Furazolidone, Nitrofurantoin, Linezolid, Bacitracin, Chloramphenicol, Daptomycin, Fosfomycin, Methenamine, Metronidazole, Mupirocin, Rifaximin, Spectinomycin |
| Anticonvulsants | Calcium Channel Modifying Agents | Includes drugs such as Nifedipine |
| | Gamma-aminobutyric Acid (GABA) Augmenting Agents | Includes drugs such as Clonazepam, Diazepam, and Phenobarbital |
| | Glutamate Reducing Agents | |
| | Sodium Channel Inhibitors | |
| Antidementia Agents | Cholinesterase Inhibitors | |
| | Glutamate Pathway Modifiers | |
| | Antidementia Agents, Other | Includes drugs such as Ergoloid Mesylates |
| Antidepressants | Monoamino Oxidase (Type A) Inhibitors | |
| | Reuptake Inhibitors | |
| | Antidepressants, Other | Includes drugs such as Bupropion, Maprotiline, Mirtazapine, Trazodone |

-continued

| Therapeutic Category | Pharmacological Class | Structural Examples |
|---|---|---|
| Antiemetics | | |
| Antifungals | | Includes drugs such as Amphotericin B, and Ketoconazole |
| Antigout Agents | | |
| Anti-inflammatories | Glucocorticoids | See Adrenal Pharmacologic Class for similar/related therapies |
| | Nonsteroidal Anti-inflammatory Drugs (NSAIDs) | See Non-opioid Analgesics Pharmacologic Class for similar/related therapies |
| Antimigraine Agents | Abortive | See Analgesics Therapeutic Category for similar/related therapies |
| | Prophylactic | See Autonomic Agents and Cardiovascular Agents Therapeutic Categories for similar/related therapies |
| Antimycobacterials | Antituberculars | Includes drugs such as Isoniazid, Pyridoxine and Cycloserine |
| | Antimycobacterials, Other | Includes drugs such as Clofazimine, Dapsone, Rifabutin |
| Antineoplastics | Alkylating Agents | Includes drugs such as Chlorambucil, Thiotepa, Busulfan, Dacarbazine, and Carmustine |
| | Antimetabolites | Includes drugs such as Methotrexate, Cytarabine, and Mercaptopurine |
| | Immune Modulators and Vaccines | Includes biotech drugs as various Monoclonal Antibodies, Cytokines, Interferones and Interleukins |
| | Molecular Target Inhibitors | Includes drugs such as Vaccines, Antisense and Gene Tharapies |
| | Nucleoside Analogues | Includes drugs such as dIdC, and AZT |
| | Protective Agents | Includes biotech drugs as Vaccines |
| | Topoisomerase Inhibitors | |
| | Antineoplastics, Other | Includes drugs such as Carboplatin, Cisplatin, Oxaliplatin |
| Antiparasitics | Anthelmintics | Includes drugs such as Mebendazole, Pyrantel Pamoate, Bithionol, and Paromomycin |
| | Antiprotozoals | Includes drugs such as Chloroquine, Pyrimethamine, Metronidazole, Furazolidone, Melarsoprol, Suramin and Tetracyclines |
| | Pediculicides/Scabicides | Includes drugs such as Crotamiton, Lindane, Benzyl Benzoate and Sulfur |
| Antiparkinson Agents | Catechol O-methyltransferase (COMT) Inhibitors | |
| | Dopamine Agonists | Includes drugs such as Levodopa, and Deprenyl |
| | Antiparkinson Agents, Other | Includes drugs such as Benztropine, Biperidin, Bromocriptine, Diphenhydramine, Procyclidine, Selegiline, Trihexyphenidyl |
| Antipsychotics | Non-phenothiazines | Includes drugs such as Chlorprothixene, and Thiothixene |
| | Non-phenothiazines/Atypicals | Includes drugs such as Haloperidol, Molindone, and Loxapine |
| | Phenothiazines | Includes drugs such as Fluphenazine |
| Antivirals | Anti-cytomegalovirus (CMV) Agents | Includes biotech drugs as Vaccines |
| | Antiherpetic Agents | Includes biotech drugs as Vaccines and Recombinant Proteins |
| | Anti-human immunodeficiency virus (HIV) Agents, Fusion Inhibitors | |
| | Anti-HIV Agents, Non-nucleoside Reverse Transcriptase Inhibitors | |
| | Anti-HIV Agents, Nucleoside and Nucleotide Reverse Transcriptase Inhibitors | |
| | Anti-HIV Agents, Protease Inhibitors | |
| | Anti-influenza Agents | Includes biotech drugs such as Vaccines, Flumist, and Thymidine Kinase Inhibitors |
| | Antivirals, Other | Includes drugs such as Adefovir and Ribavirin |
| Anxiolytics | Antidepressants | |
| | Anxiolytics, Other | Includes drugs such as Buspirone and Meprobamate |
| Autonomic Agents | Parasympatholytics | |
| | Parasympathomimetics | |
| | Sympatholytics | See Cardiovascular Agents and Genitourinary Agents Therapeutic Categories for similar/related therapies |
| | Sympathomimetics | See Cardiovascular Agents Therapeutic Category for similar/related therapies |
| Bipolar Agents | | |
| Blood Glucose Regulators | Antihypoglycemics | |
| | Hypoglycemics, Oral | |
| | Insulins | |

-continued

| Therapeutic Category | Pharmacological Class | Structural Examples |
|---|---|---|
| Blood Products/Modifiers/ Volume Expanders | Anticoagulants | Includes drugs such as Acetaminophen, Coumarin Derivatives, Aspirin, Heparin, and Indandione Derivatives |
| | Blood Formation Products | |
| | Coagulants | |
| | Platelet Aggregation Inhibitors | |
| Cardiovascular Agents | Alpha-adrenergic Agonists | See Autonomic Agents Therapeutic Category for similar/related therapies |
| | Alpha-adrenergic Blocking Agents | Includes drugs such as Phenolamine Mesylate, and Prazosin HCl |
| | Antiarrhythmics | Includes drugs such as Bretylium, Digitalis, Quinidine, and Atropine |
| | Beta-adrenergic Blocking Agents | Includes drugs such as Atenolol and related compounds |
| | Calcium Channel Blocking Agents | Includes drugs such as Nifedipine |
| | Direct Cardiac Inotropics | |
| | Diuretics | Includes drugs such as Furosemide, and Spironolactone |
| | Dyslipidermics | |
| | Renin-angiotensin-aldosterone System Inhibitors | Includes drugs such as Captopril, and Saralasin Acetate |
| | Vasodilators | Includes drugs such as Sodium Nitroprusside, Nitroglycerine |
| Central Nervous System Agents | Amphetamines | |
| | Non-amphetamines | |
| Dental and Oral Agents | | Includes such drugs as CHG |
| Dermatological Agents | Dermatological Anesthetics | Includes drugs such as Lidocaine, Dibucaine, and Diperodon |
| | Dermatological Antibacterials | Includes drugs such as Bacitracin, Chlorotetracycline, and Erythromycin |
| | Dermatological Antifungals | Includes drugs such as Haloprogin, Tolnaftate, Imidazoles, and Polyene Antibiotics |
| | Dermatological Anti-inflammatories | Includes drugs such as Hydrocortisone, Amcinonide, and Desonide |
| | Dermatological Antipruritic Agents | Includes drugs such as Benzocaine, Lidocaine, Pramoxine, Diphenhydramine, and Hydrocortisone |
| | Dermatological Antivirals | HIV-Inhibitors of reverse transcriptase (Nucleoside analogs, Non-nucleoside analogs, and Nucleotide analogs), Viral packaging inhibitors (Protease Inhibitors), Fusion Inhibitors, Herpes Virus-Nucleoside analogs (Acyclovir, Valacyclovir, Famciclovir and Penciclovir), Interferone Alpha, and Imiquimod |
| | Dermatological Keratolytics | Includes drugs such as Urea, and Salicylic Acid |
| | Dermatological Mitotic Inhibitors | Includes drugs such as Vinblastine, and Vincristine |
| | Dermatological Photochemotherapy Agents | Includes drugs such as Hydroquinone and Trioxsalen |
| | Dermatological Retinoids | Includes drugs such as Tretinoin |
| | Dermatological Tar Derivatives | Includes drugs such as Anthraquinone derivatives (Anthralin) |
| | Dermatological Vitamin D Analogs | Includes drugs such as Calcitriol, and Calcipotriol |
| | Dermatological Wound Care Agents | Includes drugs such as Collagenase, Sutilains and Dextranomers |
| | Dermatological Antiacne | Includes drugs such as Benzoyl Peroxide, and Salicylic Acid |
| | Dermatological UVA/UVB Block | Includes actives such as 3_Benzylidene_Camphors, 2-phenylbenzimidazole-5-sulfonic acid, Octyl Salicylate, Homosalate, Octylmethyl PABA,, Octyl Methoxycinnamate, Octocrylene, Oxybenzone, Menthyl Anthranilate, Titanium Dioxide, Zinc Oxide, Avobenzone |

-continued

| Therapeutic Category | Pharmacological Class | Structural Examples |
|---|---|---|
| Deterrents/Replacements Enzyme Replacements/Modifiers | Alcohol Deterrents | |
| Gastrointestinal Agents | Antispasmodics, Gastrointestinal Histamine2 (H2) Blocking Agents | Includes drugs such as Cimetidine, and Ranitidine |
| | Irritable Bowel Syndrome Agents Protectants Proton Pump Inhibitors | |
| | Gastrointestinal Agents, Other | Includes drugs such as Sevelamer, Ursodiol, Antisense, Vaccines and Mab and their fragments |
| Genitourinary Agents | Antispasmodics, Urinary | |
| | Benign Prostatic Hypertrophy Agents | See Autonomic Agents and Cardiovascular Agents Therapeutic Categories for similar/related therapies |
| | Impotence Agents | |
| | Prostaglandins | See Hormonal Agents, Stimulant/Replacement/Modifying TherapeuticCategory for similar/related therapies |
| Hormonal Agents, Stimulant/Replacement/Modifying | Adrenal | See Anti-inflammatories Therapeutic Category for similar/related therapies |
| | Parathyroid/Metabolic Bone Disease Agents Pituitary | |
| | Prostaglandins | See Genitourinary Agents Therapeutic Category for similar/related therapies |
| | Sex Hormones/Modifiers | |
| | Thyroid | Includes drugs such as Levothyroxine Sodium, and Methimazole |
| Hormonal Agents, Suppressant | Adrenal | |
| | Pituitary | Includes biotech drugs as hGH |
| | Sex Hormones/Modifiers | Includes biotech drugs as Estradiol |
| | Thyroid | |
| Immunological Agents | Immune Stimulants | Includes biotech drugs as various Monoclonal Antibodies, Interferones and Interleukins |
| | Immune Suppressants | Includes biotech drugs as various Monoclonal Antibodies, Interferones and Interleukins |
| | Immunomodulators | Includes biotech drugs as various Monoclonal Antibodies, Interferones and Interleukins |
| Inflammatory Bowel Disease Agents | Glucocorticoids | See Hormonal Agents, Stimulant/Replacement/Modifying Therapeutic Category for similar/related therapies |
| | Salicylates | |
| | Sulfonamides | See Antibacterials Therapeutic Category for similar/related therapies |
| Ophthalmic Agents | Ophthalmic Anti-allergy Agents | Includes drugs such as Cromolyn |
| | Ophthalmic Antibacterials | Includes drugs such as Bacitracin, Chloramphenicol, Erythromycin, and Polymyxin B Sulfate |
| | Ophthalmic Antifungals | Includes drugs such as Amphotericin B, Miconazole, Natamycin and Nystatin |
| | Ophthalmic Antiglaucoma Agents | Includes drugs such as Pilocarpine HCl, Carbachol, Physostigmine Salicylate, Isoflurophate, and Acetazolamide |
| | Ophthalmic Anti-inflammatories | Includes drugs such as Hydrocortisone, Dexamethasone, and Medrysone |
| | Ophthalmic Antivirals | Includes drugs such as Idoxuridine, Trifluridine, Antisense, and Vidarabine |
| | Ophthalmics, Other | Includes drugs such as Formivirsen |
| Otic Agents | Otic Antibacterials | Includes drugs such as Chloramphenicol, Neomycin Sulfate, and Polymyxins |
| | Otic Anti-inflammatories | |

| Therapeutic Category | Pharmacological Class | Structural Examples |
|---|---|---|
| Respiratory Tract Agents | Antihistamines | |
| | Antileukotrienes | |
| | Bronchodilators, Anticholinergic | |
| | Bronchodilators, Anti-inflammatories | Includes drugs such as Corticosteroid derivatives |
| | Bronchodilators, Phosphodiesterase 2 Inhibitors (Xanthines) | |
| | Bronchodilators, Sympathomimetic | Includes drugs such as Albuterol, Terbutaline, and Isoproterenol |
| | Mast Cell Stabilizers | Includes drugs such as Cromolyn Sodium |
| | Mucolytics | |
| | Respiratory Tract Agents, Other | Includes drugs such as Alpha-1-proteinase Inhibitor, Human; Benzonatate; Guaifenesin; Iodinated Glycerol; Potassium Iodide; Tetrahydrozoline |
| Sedatives/Hypnotics | | |
| Skeletal Muscle Relaxants | | Includes drugs such as Carisoprodol, Chlorphenesin Carbamate, Chlorzoxazone, and Cyclobenzaprine HCl |
| Therapeutic Nutrients/Minerals/ Electrolytes | Electrolytes/Minerals | |
| | Vitamins | |
| Toxicologic Agents | Opioid Antagonists | |

Specific compounds of interest also include, but are not limited to:

antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 476, 925, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psycopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620 5,665,752, 5,656,661, 5,635,516, 5,631,283, 5,622,948, 5,618,835, 5,607,959, 5,593,980, 5,593,960, 5,580,888, 5,552,424, 5,552,422 5,516,764, 5,510,361, 5,508,026, 5,500,417, 5,498,405, 5,494,927: 5,476,876 5,472,973 5,470,885, 5,470,842, 5,464,856, 5,464,849 5,462,952, 5,459,151, 5,451,686, 5,444,043 5,436,265, 5,432,181, RE034918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 500,654, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102; the disclosures of which are herein incorporated by reference.

Also of interest are those active agents listed in Appendix A of U.S. application Ser. No. 61/276,057 filed May 6, 2009; the disclosure of which is herein incorporated by reference.

In certain embodiments, the agent is a Resveratrol active agent. By Resveratrol active agent is meant Resveratrol, (i.e., trans-3,5,4'-Trihydroxystilbene; 3,4',5-Stilbenetriol; trans-Resveratrol; (E)-5-(p-Hydroxystyryl)resorcinol) described by the formula:

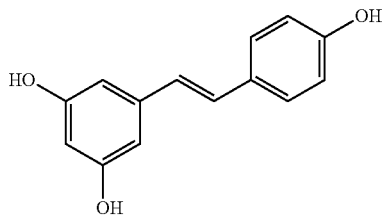 [SMILES: Oc1ccc(/C=C/c2cc(O)cc(O)c2)cc1]

or an analogue or derivative thereof, e.g., as disclosed in U.S. Pat. Nos. 7,026,518; 6,790,869 and 6,572,882; the disclosures of which are herein incorporated by reference.

In certain embodiments, the active agent is a retinol active agent, e.g., an ester of retinol (vitamin A), such as retinyl palmitate, i.e., [(2E,4E,6E,8E)-3,7-Dimethyl-9-(2,6,6-trimethyl-1-cyclohexenyl)nona-2,4,6,8-tetraenyl]hexadecanoate.

In certain embodiments, the active agent is salicylic acid, i.e., 2-Hydroxybenzoic acid.

Active agents of interest further include those listed in Appendix I to this application.

Also of interest are analogs of the above compounds.

For all of the above active agents, the active agents may be present in any convenient form. In some instances, the active agents are present in a form that is no more than sparingly soluble in water. By no more than sparingly soluble is meant that the active agent is present in a form that is water-sparingly soluble or water-insoluble. By water-sparingly soluble is meant that the agent is sparingly soluble in water. In such embodiments, the solubility of the agent in water, if any, is 0.5 g/liter or less, such as 0.25 g/liter or less, including 0.1 g/liter or less. Water-insoluble agents are agents that have substantially no solubility, if any solubility, in water. Examples of forms of active agents of interest include, but are not limited to: non-charged small molecules, peptides and high molecular weight proteins, polysaccharides and nucleic acids, etc.

In some instances, the particles are coated, such that they include a coating layer on their outer surface. Coating layers of interest include, but are not limited to, layers of material that provide for controlled release of the active agent from the particles to the environment of the particles. Coatings of interest include physiologically acceptable polymeric coatings. Materials that find use in controlled release coatings include, but are not limited to: Acrocomia Aculeata Seed Butter Almond Butter, Aloe Butter, Apricot Kernel Butter, Argan Butter, Attalea Maripa Seed Butter, Avocado Butter, Babassu Butter, Bacuri Butter, Bagura Soft Butter, Baobab Soft Butter, Bassia Butyracea Seed Butter, Bassia Latifolia Seed Butter, Black Currant Seed Butter, Brazil Nut Butter, Camelina Butter, *Camellia* Butter, Candelilla Butter, Carnauba Butter, Carpotroche Brasiliensis Seed Butter, Chamomile Butter, Cocoa Butter, Coconut Butter, Coffee Butter, Cotton Soft Butter, Cranberry Butter, Cupuacu Butter, Grape Seed Butter, Hazel Nut Butter, Hemp Seed Butter, Horsetail Butter, Illipe Butter, Irvingia Gabonensis Kernel Butter, Jojoba Butter, Karite Butter, Kokum Butter, Kukui Butter, Lavender Butter, Lemon Butter, Lime Butter, Macadamia Butter, Mango Butter, Marula Butter, Monoi Butter, Mowrah Butter, Mucaja Butter, Murumuru Butter, *Olea* Butter, Olive Butter, Orange Butter, Palm Oil, Passion Butter, Phulwara Butter, Pistachio Butter, Pomegranate Butter, Pumpkin Butter, Raspberry Butter, Rice Butter, Sal Butter, Sapucainha Butter, Seasame Butter, Shea Butter, Soy Butter Tamanu Butter, Sunflower Seed Butter, Sweet almond Butter, Tangerine Butter, Tucuma Seed Butter, Ucuuba Butter, Wheat Germ Butter, shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

Topical Compositions

Aspects of the further include topical compositions that are configured for application to a topical site of a subject. Topical compositions of the invention include: (a) uniform, rigid, spherical, nanoporous calcium phosphate particles comprising a porous structure that defines an internal space and an amount of active agent present in the internal space; and (b) a topical delivery vehicle.

Topical compositions of the invention are compositions that are formulated for delivery of an active agent to a topical location, such as a mucosal surface or keratinized skin surface of a mammalian subject, such as a human subject. By mucosal surface is meant a location of a subject that includes a mucosal membrane, such as the inside of the mouth, in the inside of the nose, etc. By keratinized skin surface is meant a skin location of a subject, i.e., a location of the external covering or integument of an animal body. Because the topical compositions of the invention are formulated for delivery to topical location, they are formulated so as to be physiologically compatible with the topical location for which they are formulated. Accordingly, when contacted with the target keratinized skin surface for which they are formulated, the topical compositions do not cause substantial, if any, physiological responses (such as inflammation or irritation) that would render the use of the topical compositions unsuitable for topical application.

As indicated above, the topical compositions include a population of active agent loaded uniform, rigid, spherical nanoporous calcium phosphate particles. In some instances, the compositions are ones in which at least some of, e.g., 10% or more, 25% or more, 50% or more, 75% or more, 80% or more, 90% or more by weight, including substantially all of, e.g., 95% or more, 97% or more, 99% or more, by weight of the particles of the composition include an internal amount of active agent. The amount of active agent component (which is made up of one or more distinct active agents) that is bound to the particles may vary depending on the particular active agent(s) making up the active agent bound particles, and in certain embodiments ranges from 0.01 to 2000 mg/g, such as from 0.1 to 1000 mg/g and including 1 to 300 mg/g active agent(s)/gram particle.

In a given topical composition of the invention, a distribution of diameters for the particles thereof may be present, where in some instances the majority (such as 60% or more, 75% or more, 90% or more, 95% or more) of the particles have diameters that range from 0.01 to 20 µm, such as from 0.1 to 10 µm, and including from 0.1 to 2 µm. In some instances, the proportion of the particles that have an average particle diameter of 2 µm or less is 50% or more by number, such as 70% or more by number, including 90% or more by number.

As indicated above, the topical compositions of the invention further include a topical delivery vehicle. The delivery vehicle (i.e., topical delivery component) refers to that portion of the topical composition that is not the active agent loaded particles. The amount of active agent loaded particles that is present in the delivery composition and therefore combined with a delivery vehicle may vary. In some embodiments, the amount of active agent loaded particles present in the delivery vehicle ranges from 0.01 to 200 mg/g, such as 0.1 to 100 mg/g and including 1 to 50 mg/g active agent loaded particles per gram of delivery vehicle. In certain embodiments the particles are present in compositions in an amount ranging from about 0.001 to about 80% by weight, such as from about 0.01 to about 70% by weight, and including from about 0.05 to about 60% by weight.

Delivery vehicles of interest include, but are not limited to, compositions that are suitable for delivery via one or more of oral, topical, injection, implantation, ocular, aural, rectal, vaginal, etc., routes. In certain embodiments, the vehicle is formulated for application to a topical region or surface of a subject, such as a keratinized skin surface. The subject compositions may be formulated as stable solutions or suspensions of the components, e.g., in an aqueous solvent. Where desired, the components may be combined with one or more carrier materials to form a solution, suspension, gel, lotion, cream, ointment, aerosol spray or the like, as desired. Of interest in certain embodiments are aqueous delivery vehicles, i.e. aqueous vehicles that include a certain amount of water. Examples of aqueous vehicles include hydrogel vehicles, sprays, serums, etc.

The topical composition may also contain other physiologically acceptable excipients or other minor additives, particularly associated with organoleptic properties, such as fragrances, dyes, buffers, cooling agents (e.g. menthol), stabilizers or the like. The excipients and minor additives will be present in conventional amounts, e.g., ranging from about 0.001% to 5%, such as 0.001-2%, by weight, and in some instances not exceeding a total of 10% by weight.

As indicated above, of interest in certain embodiments are semi-solid delivery compositions, such as gels, creams and ointments. Such compositions may be mixtures of (in addition to the active agent) water, water soluble polymers, preservatives, alcohols, polyvalent alcohols, emulsifying agents, wax, solvents, thickeners, plasticizers, pH regulators, water-retaining agents and the like. Furthermore, such compositions may also contain other physiologically acceptable excipients or other minor additives, such as fragrances, dyes, buffers, stabilizers or the like.

Also of interest are solid formulations, such as topical patch formulations. Topical patch formulations may vary significantly. Topical patch formulations may include an active agent layer, a support and a release liner. The active agent layer may include physiologically acceptable excipients or other minor additives, such as fragrances, dyes, buffers, stabilizers or the like. The support may be made of a flexible material which is capable of fitting in the movement of human body and includes, for example, plastic films, various non-woven fabrics, woven fabrics, spandex, and the like. Various inert coverings may be employed, which include the various materials which may find use in plasters, described below. Alternatively, non-woven or woven coverings may be employed, particularly elastomeric coverings, which allow for heat and vapor transport. These coverings allow for cooling of the pain site, which provides for greater comfort, while protecting the gel from mechanical removal. The release liner may be made of any convenient material, where representative release films include polyesters, such as PET or PP, and the like.

Embodiments of the compositions exhibit greater stability with respect to UV light, including both UVA and UVB light, as compared to other formulations of the active agent, e.g., formulations in which a calcium phosphate particle is not present in the composition. As such, compositions of the invention exhibit reduced sensitivity to UV light compared to a suitable control, as determined using any convenient UV light sensitivity assay.

Embodiments of the compositions exhibit greater pH stability as compared to other formulations of the active agent, e.g., formulations in which a calcium phosphate particle is not present in the composition. As such, compositions of the invention exhibit reduced sensitivity to pH compared to a suitable control, as determined using any convenient pH sensitivity assay. In certain embodiments, the compositions are stable at pH ranging from 3 to 11, e.g., 4 to 11, such as 4.25 to 10.75.

Embodiments of the compositions exhibit greater stability with respect to oxidation, as compared to other formulations of the active agent, e.g., formulations in which a calcium phosphate particle is not present in the composition. As such, compositions of the invention exhibit reduced sensitivity to oxidation compared to a suitable control, as determined using any convenient oxidation sensitivity assay.

Embodiments of the compositions exhibit greater stability with respect to thermal degradation, as compared to other formulations of the active agent, e.g., formulations in which a calcium phosphate particle is not present in the composition. As such, compositions of the invention exhibit reduced sensitivity to thermal degradation compared to a suitable control, as determined using any convenient thermal degradation sensitivity assay.

Embodiments of the compositions exhibit greater stability with respect to mechanical degradation, as compared to other formulations of the active agent, e.g., formulations in which a calcium phosphate particle is not present in the composition. As such, compositions of the invention exhibit reduced sensitivity to mechanical degradation compared to a suitable control, as determined using any convenient mechanical degradation sensitivity assay.

Fabrication Methods

Aspects of the invention further include methods of making the active agent loaded uniform, rigid, spherical, nanoporous calcium phosphate particles and topical compositions that include the same. With respect to methods of making the active agent loaded uniform, rigid, spherical, nanoporous calcium phosphate particles, aspects of these methods include combining an amount of uniform, rigid, spherical, nanoporous calcium phosphate particles comprising a porous structure that defines an internal space; and an active agent. The particles and active agent are combined in the presence of a non-aqueous solvent under conditions sufficient for the active agent to enter internal space of the uniform, rigid, spherical, nanoporous calcium phosphate particles to produce active agent loaded uniform, rigid, spherical, nanoporous calcium phosphate particles. This step results in the production of a liquid composition that includes an amount of active agent loaded uniform, rigid, spherical, nanoporous calcium phosphate particles present in a non-aqueous solvent, which may include one or more co-solvents. Following this combination step, the methods include separating the non-aqueous solvent from the active agent loaded uniform, rigid, spherical, nanoporous calcium phosphate particles to produce a dry product composition, i.e. a powder that is made up of active agent loaded uniform, rigid, spherical, nanoporous calcium phosphate particles.

In some instances, the methods include pre-wetting an initial amount of uniform, rigid, spherical, nanoporous calcium phosphate particles with a non-aqueous solvent to remove gas present inside of the uniform, rigid, spherical, nanoporous calcium phosphate particles. For example, an amount of particles may be combined with a non-aqueous organic solvent under conditions sufficient to produce wetted particles. The protocol employed for combining the particles with the non-aqueous solvent may vary, where examples of protocols of interest include, immersion, with or without agitation, etc. Solvents of interest include, but are not limited to: cosmetic or dermopharmaceutical solvents such as, but not limited to: ethanol, propanol, isopropanol, propylene glycol, glycerin, butylene glycol, ethoxydiglycol, polyethylene glycol, methyl or ethyl ethers of diglycols, cyclic polyols, ethoxylated or propoxylated glycols and solvent listed in USP 467 Residual Solvents—Class 3 Residual Solvents such as Acetic acid Heptane, Acetone, Isobutyl acetate, Anisole, Isopropyl acetate, 1-Butanol, Methyl acetate, 2-Butanol, 3-Methyl-1-butanol, Butyl acetate, Methylethylketone, tert-Butylmethyl ether, Methylisobutylketone, Cumene, 2-Methyl-1-propanol, Dimethyl sulfoxide, Pentane, Ethanol, 1-Pentanol, Ethyl acetate, 1-Propanol, Ethyl ether, 2-Propanol, Ethyl formate, Propyl acetate, Formic acid and solvent listed in USP 467—Class 2 Residual Solvents such as Acetonitrile, Chlorobenzene, Chloroform, Cyclohexane, 1,2-Dichloroethene, 1,2-Dimethoxyethane, N,N-Dimethylacetamide, N,N-Dimethylformamide, 1,4-Dioxane, 2-Ethoxyethanol, Ethylene glycol, Formamide, Hexane, Methanol, 2-Methoxyethanol, Methylbutylketone, Methylcyclohexane, Methylene chloride, N-Methylpyrrolidone, Nitromethane, Pyridine, Sulfolane, Tetrahydrofuran, Tetralin, Toluene, Trichloroethylene, and Xylene. Following combination, excess solvent may be separated from the particles as desired to produce the wetted particles.

The particles (either dry or pre-wetted as described above) may be combined with a solution of an active agent present in a non-aqueous (e.g., organic) solvent to produce a liquid composition that includes particles and an active agent(s) in a non-aqueous, e.g., organic, solvent. The non-aqueous, e.g., organic, solvent of the active agent solution may vary. Solvents of interest include, but are not limited to: cosmetic or dermopharmaceutical solvents such as, but not limited to: ethanol, propanol, isopropanol, propylene glycol, glycerin, butylene glycol, ethoxydiglycol, polyethylene glycol, methyl or ethyl ethers of diglycols, cyclic polyols, ethoxylated or propoxylated glycols and solvent listed in USP 467 Residual Solvents—Class 3 Residual Solvents such as Acetic acid Heptane, Acetone, Isobutyl acetate, Anisole, Isopropyl acetate, 1-Butanol, Methyl acetate, 2-Butanol, 3-Methyl-1-butanol, Butyl acetate, Methylethylketone, tert-Butylmethyl ether, Methylisobutylketone, Cumene, 2-Methyl-1-propanol, Dimethyl sulfoxide, Pentane, Ethanol, 1-Pentanol, Ethyl acetate, 1-Propanol, Ethyl ether, 2-Propanol, Ethyl formate, Propyl acetate, Formic acid and solvent listed in USP 467—Class 2 Residual Solvents such as Acetonitrile, Chlorobenzene, Chloroform, Cyclohexane, 1,2-Dichloroethene, 1,2-Dimethoxyethane, N,N-Dimethylacetamide, N,N-Dimethylformamide, 1,4-Dioxane, 2-Ethoxyethanol, Ethylene glycol, Formamide, Hexane, Methanol, 2-Methoxyethanol, Methylbutylketone, Methylcyclohexane, Methylene chloride, N-Methylpyrrolidone, Nitromethane, Pyridine, Sulfolane, Tetrahydrofuran, Tetralin, Toluene, Trichloroethylene, and Xylene. The solvent may be the same as or different from the solvent employed to wet the particles. If different, in certain embodiments, the solvent of the active agent solution is at least miscible with the solvent employed to wet the particles. The active agent solution may include one or more cosolvents, where cosolvents of interest include, but are not limited to: polyethylene glycols, e.g., PEG 400, PEG 200, etc., glycerides, etc.

The active agent solution and particles (dry or pre-wetted, as desired) may be combined using any convenient protocol, e.g., with agitation, to produce a liquid composition that includes both the particles and the active agent. In certain instances, the uniform, rigid, spherical, nanoporous calcium phosphate particles and active agent are combined in the presence of the non-aqueous solvent under controlled pressure. When combined under controlled pressure, pressures of interest may vary and in some instances range from 0.001 torr to 1 torr, such as 0.01 torr to 0.1 torr and including 0.05 torr to 0.5 torr.

Next, the non-aqueous solvent is separated from the particles of the liquid composition to produce the desired product of uniform, rigid, spherical, nanoporous calcium phosphate particles comprising a porous structure that defines an internal space and an amount of active agent present in the internal space. Separation may be accomplished using any convenient protocol, where in certain embodiments the separation includes drying under negative pressure, e.g., in a vacuum, via a vacuum desiccator, vacuum dryer, spray dryer, rotary evaporator, etc. Where desired, elevated temperatures may be employed in this separation step.

The above fabrication protocol results in the production of a dry powder composition that includes active agent loaded uniform, rigid, spherical, nanoporous calcium phosphate particles, i.e., uniform, rigid, spherical, nanoporous calcium phosphate particles that include a porous structure which defines an internal space and an amount of active agent present in the internal space.

To produce topical compositions as described above, an amount of the resultant active agent loaded uniform, rigid, spherical, nanoporous calcium phosphate particles may be combined with a delivery vehicle of interest as desired. Convention fabrication protocols may be employed.

Utility

Topical compositions of the invention find use in methods of delivering active agents to a topical location of a subject, where the topical location may be a skin surface location or a mucosal location. In delivering active agents to a topical location of a subject, formulations of the invention may deliver the active agent loaded particles at least into an epidermal location that is beneath the skin surface of a subject. As such, embodiments of the invention include methods of delivering active agent loaded particles into the stratum corneum of a subject, where the methods may result in delivery of the complexes into the deep stratum corneum and/or dermis of a subject. By “deep stratum corneum” is meant a region that is 2 or more cell layers below the skin surface, such as 5 or more cell layers below the skin surface, including 10 or more cell layers below the skin surface. In some instances, the complexes are delivered to region of the stratum corneum that is 2 μm or more such as 5 μm or more and including 15 μm or more below the surface of the skin.

Upon reaching their target dermal location, the active agent loaded particles begin to release their active agent “payload” and break down (e.g., via dissolution caused by pH gradient of the skin), as the uniform, rigid, spherical, nanoporous particles dissolve under acidic conditions, e.g., conditions of pH 6 or lower, such as 5.5 or lower, including 5.0 or lower, such as the physiological acidic conditions of the stratum corneum. The time required for dissolution of particles in the stratum corneum may vary, and in certain embodiments ranges from 1 minute to 24 hours, such as 10 minutes to 12 hours and including 30 minutes to 3 hours, over which time period active agent is released from the active agent bound particles. The proportion of active agent that is released from the active agent bound particles may vary, and in certain instances is 1% or more, such as 10% or more, including 50% or more (w/w).

Methods of the invention may therefore result in delivery of an active agent at least into the stratum corneum of a subject. In some embodiments, the active agent remains in the stratum corneum to exert its desired activity. In yet other embodiments, active agent may exert its desired activity at one or more other target locations of the body. Additional target locations of the body of interest include additional epidermal regions, such as but not limited to the stratum lucidum, stratum granulosum, stratum spinusom, stratum basale and dermis. In certain embodiments, the active agent is delivered to a region of the dermis. In certain embodiments, the active agent is delivered to a region below the dermis, e.g., into sub-cutaneous tissues. Depending on the location which is contacted by the active agent upon delivery with the dermal delivery formulations of the invention, in some instances the active agent may be systemically delivered to the subject. When the active agent is systemically delivered to the subject, therapeutic plasma levels of active agent are achieved. Therapeutic plasma levels of active agent may vary depending on the particular active agent and condition being treated. In certain embodiments, therapeutic active levels that are achieved range from 1 pg to 20 μg, such as 1 ng to 1 μg and including 10 ng to 100 ng.

In practicing methods of the invention, a topical composition is applied to a topical region of a subject and maintained at the topical region for a period of time sufficient to result in the desired delivery of active agent to the subject, as described above. The topical region is, in certain embodiments, a keratinized skin region. The keratinized skin region, including hair follicles, sweat glands and sebaceous glands, may be present at a variety of locations, e.g., limbs, arms, legs; torso, e.g., chest, back, stomach; head, e.g., neck, face; etc. In certain embodiments, the region will be a head region, such as a facial region, e.g., forehead, occipital region, around the mouth, etc. The topical region to which the composition is applied may vary with respect to area, ranging in certain embodiments from 1 $mm^2$ to 300 $cm^2$ or more, such as from 1 to 50 $cm^2$, and including from 3 to 10 $cm^2$.

Following application, the topical is maintained at the site of application for a period of time sufficient for a desired therapeutic outcome to occur, e.g., amelioration of a symptom(s) of interest, reducing dryness. The period of time may vary, and in certain embodiments ranges from 1 min to 24 hours or longer, such as from 30 min to 12 hours and including from 1 hour to 12 hours or longer.

In practicing the methods of the invention, a subject may be administered a single dose or two or more doses over a given period of time. For example, over a given treatment period of one month, 1 or more doses, such as 2 or more doses, 3 or more doses, 4 or more doses, 5 or more doses, etc., may be administered to the subject, where the doses may be administered weekly or daily or even multiple times per day.

In some instances, methods of the invention result in enhanced penetration of the active agent as compared to a suitable control, such as a composition made up of the same active agent and delivery vehicle, with the exception that the active agent is not loaded into uniform, rigid, spherical, nanoporous calcium phosphate particles. Penetration is enhanced in such embodiments as compared to a control by a factor of 2-fold or more, such as 5-fold or more, including 10-fold or more.

The subject methods and compositions may be used in a variety of different kinds of animals, where the animals are typically “mammals” or “mammalian,” where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects or patients are humans.

The subject topical formulations find use in applications where it is desired to deliver an active agent to a subject. In certain embodiments, the subject topical formulations are employed in the treatment of a disease condition, e.g. a disease condition responsive to administration of the active agent. By "treatment" is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the subject no longer suffers from the condition, or at least the symptoms that characterize the condition. In certain embodiments a subject may be diagnosed for the presence of the disease condition, such that the topical formulations are provided to a subject known to be suffering from the disease condition The following examples are offered by way of illustration and not by way of limitation.

EXPERIMENTAL

I. Fabrication and Characterization of Uniform, Rigid, Spherical, Nanoporous Calcium Phosphate Particles A. Fabrication Calcium phosphate nano crystal slurry was prepared by dropwise addition of aqueous phosphate complex solution to aqueous calcium complex solution or suspension under controlled conditions of temperature, pH, stirring velocity, reagent concentration, addition rate and aging time. The slurry was spray dried to form spherical porous powder by using a pressure nozzle type spray dryer with an air-liquid fluids nozzle. The dried powder was sintered at temperature ranging 300 to 900° C. for a period of time ranging 1 to 24 hours with gas kiln or an electric furnace.

B. Characterization

Figure 1B:
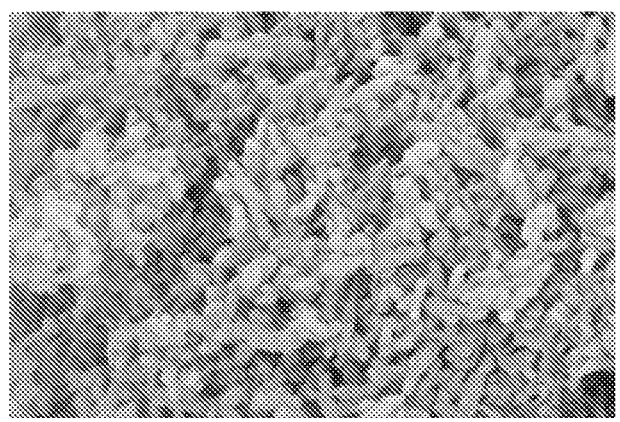
Figure 2A:
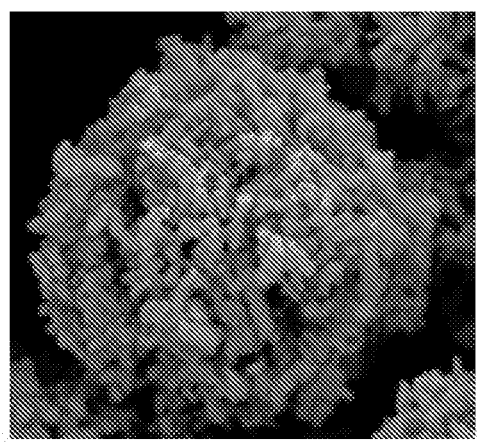
Figure 2B:
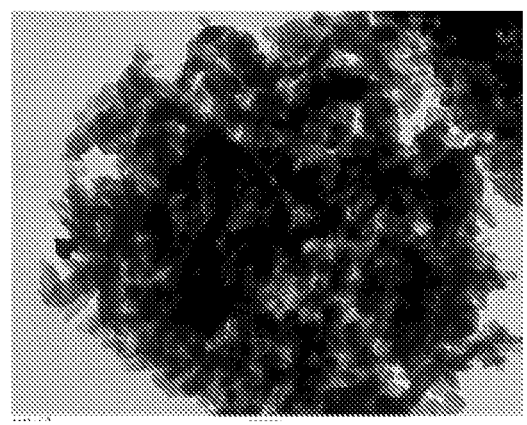
Figure 3:
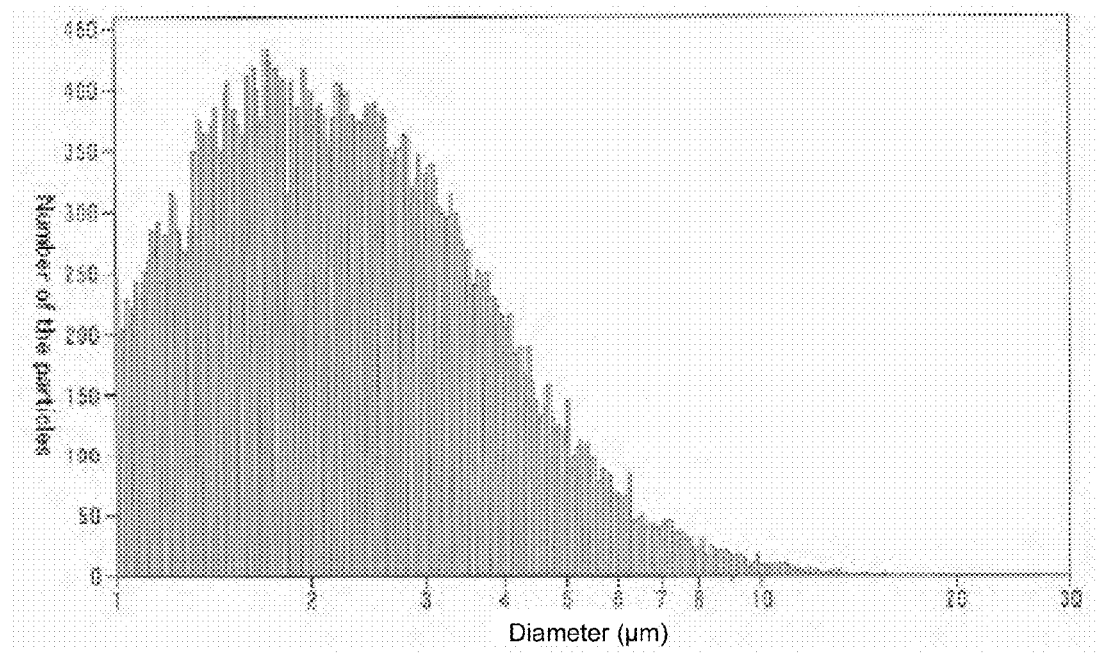
FIG. 3 provides a graphical representation of the particle size distribution of uniform, rigid, spherical, nanoporous calcium phosphate particles that find use in delivery compositions of the invention.

FIGS. 1A and 1B show the porous structure of the resultant 2 micron uniform, rigid, spherical, nanoporous calcium phosphate particles (produced in as described above) using SEM (A) 10,000×, (B) 50,000×. FIGS. 2A and 2B show the outside and inside structure of 2 micron uniform, rigid, spherical, nanoporous calcium phosphate particles (produced in as described above) using both SEM (A) and TEM (B) (15000×). The large (25-50 m$^2$/g) internal and external surface areas are substantial, allowing for high capacity binding with active agents. FIG. 3 shows the particle size distribution of the particles, as determined by Coulter Multisizer 3 particle counter and confirmed by scanning electron microscopy. The average particle size was 2 μm.

II. Active Agent Loading of Uniform, Rigid, Spherical, Nanoporous Calcium Phosphate Particles A. Salicylic Acid Salicylic acid, a hydrophobic small molecule useful for anti-acne agent, is water insoluble and shows low binding capacity to hydroxyapatite (having a binding capacity to hydroxyapatite of about 1 mg or less). Salicylic acid is soluble in ethanol and PEG (poly ethylene glycol) up to 30%. Hydroxyapatite is soluble and degrades in acidic solution.

As illustrated below, when the ratio of HYDROXYSOMES® uniform, rigid, spherical nanoporous calcium phosphate particles (Laboratory Skin Care, Olympic Valley Calif.) and solid salicylic acid is small enough to prevent dissolution of the calcium phosphate particles, a highly loaded salicylic acid and calcium phosphate particle dry powder composite can be obtained by removing the solvent after a soaking and penetration process under vacuum pressure, as described in greater detail below.

The following raw materials were used for making 25% Salicylic acid loaded HYDROXYSOMES® uniform, rigid, spherical nanoporous calcium phosphate particles complex.

| Salicylic Acid | 17.24% | 12.50 g |
|---|---|---|
| PEG-8 | 13.80% | 10.00 g |
| Hydroxysomes ® (uniform, rigid, spherical nanoporous calcium phosphate particles) | 68.96% | 50.00 g |
| TOTAL: | 100.00% | 72.50 g |

Solvent: Ethanol was used.

Procedure:
1. Prepare particle suspension by soaking HYDROXYSOMES® uniform, rigid, spherical nanoporous calcium phosphate particles with 89 g of Ethanol for 30 minute with or without vacuum.
2. Prepare Salicylic Acid saturated solution by mixing Salicylic Acid, PEG-8 and 81 g of ethanol in the beaker until mixture becomes homogeneous.
3. Mix HYDROXYSOMES® uniform, rigid, spherical nanoporous calcium phosphate particles suspension and Salicylic acid solution for 30 minutes
4. Remove ethanol by using the rotary evaporator under vacuum at 600 mmHg for 2 h 30 minutes.
5. The dry powder complex was obtained.

B. Salicylic Acid without Co-Solvent

The following raw materials were used for making 20% Salicylic acid loaded HYDROXYSOMES® uniform, rigid, spherical nanoporous calcium phosphate particles suspension complex.

| Salicylic Acid | 20% | 1 g |
|---|---|---|
| Hydroxysomes ® (uniform, rigid, spherical nanoporous calcium phosphate particles) | 80% | 4 g |
| TOTAL: | 100% | 5 g |

Solvent: 10 g of Ethanol was used.

Procedure:
1. Prepare Salicylic Acid saturated solution by mixing Salicylic Acid and 10 g of ethanol in the beaker until it become homogeneous.
2. Add HYDROXYSOMES® uniform, rigid, spherical nanoporous calcium phosphate particles suspension into Salicylic acid solution
3. Remove ethanol by using the rotary evaporator under vacuum at 600 mm Hg for 1 h 30 minutes. Starting pressure was 173 mbar and the final pressure was 30 mbar.
4. The dry powder complex was obtained.

C. Resveratrol

Resveratrol loaded HYDROXYSOMES® uniform, rigid, spherical nanoporous calcium phosphate particles were prepared as described above in Example I. The following raw materials were used for making 20% Resveratrol loaded HYDROXYSOMES® uniform, rigid, spherical nanoporous calcium phosphate particles complex.

| Resveratrol | 20% | 2.5 g |
|---|---|---|
| Hydroxysomes ® (uniform, rigid, spherical nanoporous calcium phosphate particles) | 80% | 10 g |
| TOTAL: | 100% | 12.5 g |

Solvent: 38 g of Ethanol was used.

Procedure:
1. Prepare HYDROXYSOMES® uniform, rigid, spherical nanoporous calcium phosphate particle suspension by soaking HYDROXYSOMES® uniform, rigid, spherical nanoporous calcium phosphate particles with 18 g of Ethanol for 30 minute under vacuum condition with a diaphram vacuum pump.
2. Prepare Resveratrol solution by mixing Resveratrol and 20 g of ethanol in the beaker until it becomes homogeneous.
3. Mix HYDROXYSOMES® uniform, rigid, spherical nanoporous calcium phosphate particle suspension and Resveratrol solution for 30 minutes
4. Remove ethanol by using the rotaly evaporator (Buchi Rotavapor R-215) under vacuum 85 mbar at 40° C. for 8 hr.
5. The dry powder Resveratrol complex was obtained.

The maximum amount of the Resveratrol complex produce above that could be dissolved in an aqueous formulation was compared with free Resveratrol. It as found that seven times higher amount of Resveratrol can be uniformly dispersed and formulated in the aqueous formulation as compared to free Resveratrol.

D. Retinyl Palmitate

Retinyl Palmitate loaded HYDROXYSOMES® uniform, rigid, spherical nanoporous calcium phosphate particles were prepared as described above in Example I. The following raw materials were used for making 16.7% Retinyl Palmitate loaded HYDROXYSOMES® uniform, rigid, spherical nanoporous calcium phosphate particle complex.

| Retinyl Palmitate | 16.7% | 10 g |
|---|---|---|
| Hydroxysomes ® (uniform, rigid, spherical nanoporous calcium phosphate particles) | 83.3% | 50 g |
| TOTAL: | 100% | 60 g |

Solvent: 280 g of Ethanol was used.

Procedure:
1. Prepare HYDROXYSOMES® uniform, rigid, spherical nanoporous calcium phosphate particle suspension by soaking HYDROXYSOMES® uniform, rigid, spherical nanoporous calcium phosphate particles with 80 g of Ethanol for 30 minute under vacuum condition with a diaphragm vacuum pump.
2. Prepare Retinyl Palmitate solution by mixing Retinyl Palmitate and 200 g of ethanol in the beaker until it becomes homogeneous.
3. Mix HYDROXYSOMES® uniform, rigid, spherical nanoporous calcium phosphate particle suspension and Retinyl Palmitate solution for 30 minutes
4. Remove ethanol by using the rotary evaporator (Buchi Rotavapor R-215) under vacuum 75 mbar at 40° C. for 8 hr.
5. The dry powder Retinyl Palmitate complex was obtained.

The resultant Retinyl Palmitate HYDROXYSOMES® uniform, rigid, spherical nanoporous calcium phosphate particles were successfully formulated as a complex in an aqueous formulation.

E. Example of the Other Water Insoluble Actives

Lipophilic actives such as, Polyphenol, Carotinoide, Flavonoide, Anthocyane, Vitamin A, Vitamin E, Astaxanthin, Argireline, (Dipalmitoyl hydroxyproline), Ubiquinol, lipophilic drugs such as Adapalene, Duclofenac, Lidokine can be loaded on HYDROXYSOMES® uniform, rigid, spherical nanoporous calcium phosphate particles according to the methods described above.

Figure 4:
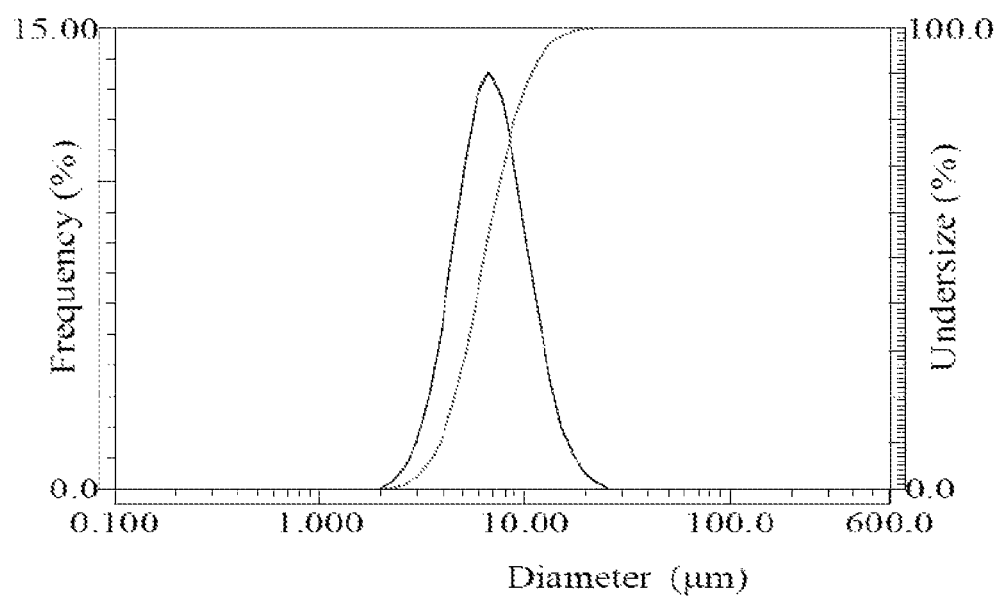
FIG. 4 provides a graphical representation of the particle size distribution of uniform, rigid, spherical, nanoporous calcium phosphate particles complexed with resveratrol, according to an aspect of the invention.

III. Characterization of Active Agent Loaded Uniform, Rigid, Spherical, Nanoporous Calcium Phosphate Particles A. Particle Size Distribution The particle size distribution of the Resveratrol loaded Hydroxysomes® Complex as produced above was evaluated by using Horiba LA-300 laser particle size analyzer. Both Hydroxysomes® and the Resveratrol complex showed weight base average particle size about 6 µm with uniform particle size distribution, as shown in FIG. 4.

B. Mechanical Stability

The mechanical stability of Hydroxysomes® and the Resveratrol Hydroxysomes® complex and were measured by using Shimadzu MCT micro-compression tester. There was no change of the breaking point force between Hydroxysomes® and the Resveratrol Hydroxysomes® complex. The mechanical stability of the Resveratrol Hydroxysomes® complex during the homogenizing process and mixing process were evaluated by using Horiba LA-300 laser particle analyzer. There was no particle size change after the processing.

C. Microscopy

Figure 5:
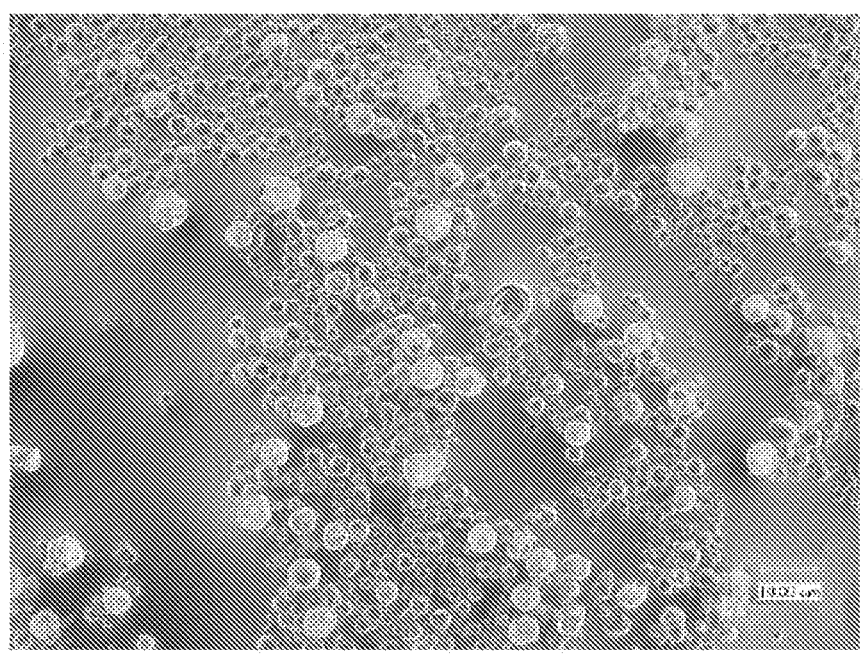
FIG. 5 shows a microscopic view of a uniform, rigid, spherical, nanoporous calcium phosphate particles complexed with resveratrol, according to an aspect of the invention.

The microscopic observation showed the spherical uniform structure of the Resveratrol Hydroxysomes® complex as shown in FIG. 5.

D. Loading Confirmation

The reverse phase HPLC analysis of the methanol extraction of the Resveratrol Hydroxysomes® complex showed the actual loaded amount of the Resveratrol in the complex as follows.

| Sample | Resveratrol content |
|---|---|
| 15% Loaded (15:85 Resveratrol:Hydroxysomes ®) | 13.04% |
| 20% Loaded (20:80 Resveratrol:Hydroxysomes ®) | 16.67% |
| 25% Loaded (20:57 Resveratrol:Hydroxysomes ®) | 20.00% |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A composition comprising:
   uniform, rigid, spherical, nanoporous calcium phosphate particles comprising a porous structure that defines an internal space; and
   an amount of active agent that is no more than sparingly soluble in water present in the internal space, wherein the amount of active agent present in the internal space is 10% by weight or more of the calcium phosphate particle.

2. The composition according to claim 1, wherein the uniform, rigid, spherical, nanoporous calcium phosphate particle is ceramic.

3. The composition according to claim 1, wherein the uniform, rigid, spherical, nanoporous calcium phosphate particle comprises pores ranging in size from 2 nm to 100 nm.

4. The composition according to claim 1, wherein the active agent is a retinol.

5. The composition according to claim 1, wherein the particle is coated with a material different from the active agent.

6. The composition according to claim 1, wherein the active agent is a resveratrol active agent.

7. The composition according to claim 1, wherein 60% or more of the particles have a diameters ranging from 0.1 to 2 μm.

8. The composition according to claim 1, wherein the composition consists of:
   the uniform, rigid, spherical, nanoporous calcium phosphate particles comprising a porous structure that defines an internal space; and
   the amount of active agent that is no more than sparingly soluble in water present in the internal space, wherein the amount of active agent present in the internal space is 10% by weight or more of the calcium phosphate particle.

9. A composition comprising:
   uniform, rigid, spherical, nanoporous calcium phosphate particles comprising a porous structure that defines an internal space and an amount of active agent that is no more than sparingly soluble in water present in the internal space, wherein the amount of active agent present in the internal space is 10% by weight or more of the calcium phosphate particle and the particles are prepared by the method comprising:
   (a) combining:
   uniform, rigid, spherical, nanoporous calcium phosphate particles comprising a porous structure that defines an internal space; and
   an active agent;
   in the presence of a non-aqueous solvent under conditions sufficient for the active agent to enter internal space of the uniform, rigid, spherical, nanoporous calcium phosphate particles to produce active agent loaded uniform, rigid, spherical, nanoporous calcium phosphate particles; and
   (b) separating the non-aqueous solvent from the active agent loaded uniform, rigid, spherical, nanoporous calcium phosphate particles.

10. The composition according to claim 9, wherein the method comprises pre-wetting the uniform, rigid, spherical, nanoporous calcium phosphate particles with a non-aqueous solvent to remove gas present inside of the uniform, rigid, spherical, nanoporous calcium phosphate particles.

11. The composition according to claim 9, wherein the uniform, rigid, spherical, nanoporous calcium phosphate particles and active agent are combined in the presence of the non-aqueous solvent under pressure.

12. The composition according to claim 9, wherein the non-aqueous solvent is an organic solvent.

13. The composition according to claim 9, wherein the organic solvent comprises an organic co-solvent.

14. The composition according to claim 9, wherein the non-aqueous solvent is separated from the active agent loaded uniform, rigid, spherical, nanoporous calcium phosphate particles by evaporating the non-aqueous solvent.

15. The composition according to claim 14, wherein the evaporating occurs under negative pressure.

16. The composition according to claim 9, wherein the active agent is a retinol active agent.

* * * * *